United States Patent [19]

Aarnio et al.

[11] Patent Number: 5,107,843
[45] Date of Patent: Apr. 28, 1992

[54] METHOD AND APPARATUS FOR THIN NEEDLE BIOPSY IN CONNECTION WITH MAMMOGRAPHY

[75] Inventors: Jaakko A. Aarnio, Helsinki; Terho Turkumaki, Sipoo, both of Finland

[73] Assignee: Orion-Yhtyma Oy, Espoo, Finland

[21] Appl. No.: 680,872

[22] Filed: Apr. 5, 1991

[30] Foreign Application Priority Data

Apr. 6, 1990 [FI] Finland ................... 90 1768

[51] Int. Cl.⁵ .............................. A61B 8/14
[52] U.S. Cl. .................. 128/662.05; 128/754
[58] Field of Search .............. 128/662.05, 664, 665, 128/749, 754, 755

[56] References Cited

U.S. PATENT DOCUMENTS

| | | | |
|---|---|---|---|
| 4,058,114 | 11/1977 | Soldner | 128/754 |
| 4,346,717 | 8/1982 | Haerten | 128/662.05 |
| 4,635,644 | 1/1987 | Yagata | 128/662.05 |
| 4,671,292 | 6/1987 | Matzuk | 128/662.05 |
| 4,681,103 | 7/1987 | Boner et al. | 128/754 |

Primary Examiner—Max Hindenburg
Attorney, Agent, or Firm—Browdy and Neimark

[57] ABSTRACT

The invention relates to a method for thin needle biopsy in connection with mammography, wherein a stationary target is radiographed from two angles by means of a rotating picture head, the pictures are placed on a separate measurement table, and the x-, y-, and z-coordinates of the desired site in the target are calculated on the basis of the two pictures in a known manner. In the method, measuring means (3,4) on the measuring table are brought to the calculated x-, y-coordinates and a detachable needle guide (10) is placed in an attachment means (6) on the measurement table and the needle guide (10) is adjusted to these coordinates indicated by the measuring means (3,4), and the z-coordinate is adjusted by means of a scale in the needle guide (10), whereafter the adjusted needle guide is attached to the attachment means (9) in the mammography apparatus, the attachment means being in the same position with respect to the calculated coordinates as is the attachment means (6) on the measurement table, and a biopsy is carried out by pressing the needle manually into the target. The invention also relates to an assembly for embodying the method.

4 Claims, 3 Drawing Sheets ed. The pictures so obtained are placed onto a separate measurement table, and the x-, y-, and z-coordinates of the desired site in the target are calculated in a known manner on the basis of the two pictures. Thereafter the measuring means on the measurement table are brought to the calculated x-, y-coordinates, and the detachable needle guide is placed in a fixed attachment means in the measurement table, and the needle guide is adjusted to these coordinates indicated by the measuring means. The z-coordinate is adjusted, for example, with the help of a scale in the needle guide. Thereafter the pre-adjusted needle guide is attached to the mammography apparatus and the specimen is taken by pressing the needle manually into the target.

METHOD AND APPARATUS FOR THIN NEEDLE BIOPSY IN CONNECTION WITH MAMMOGRAPHY

FIELD OF THE INVENTION

A method for thin needle biopsy or tissue marking in connection with mammography, and an assembly for carrying out the method.

BACKGROUND OF THE INVENTION

The invention relates to a method for thin needle biopsy or tissue marking of a patient's mammary gland in connection with mammography, and an assembly which enables a suspect site in the tissue to be localized and a thin needle biopsy specimen to be taken of it. In the method, a stationary target is radiographed from two angles by means of a rotating picture head, the pictures are placed on a separate measurement table, and the x, y and z coordinates of the desired site in the target are calculated in a known manner on the basis of the two pictures.

Especially in connection with mammographic examinations it is often necessary to localize some interesting site in the target, for example for biopsy. In connection with mammography, usually thin needle biopsy is used, for example for the diagnosis of cancer. Furthermore, in connection with thin needle biopsy it is possible to mark the interesting site with a thin thread in order to facilitate a surgical operation following the biopsy. The method used for localizing the target is known per se. WP publication 88/01847 describes a method and apparatus for stereotactic biopsy of pathological sites in the breast. In the method, the target is radiographed from two directions, and the location of the pathological site is determined on the basis of these two pictures. In this method the picture head and the film are maintained stationary, and the target is moved in the horizontal direction in order to obtain a pair of pictures. The method is inconvenient for the patient, and the accuracy of the method may suffer as the patient has to move between the taking of the pictures.

EP Patent Application 0146511 also presents a method for the localization of a three-dimensional target point within the target by using X-rays. In this method the target is radiographed from two directions, and on the basis of these pictures the location coordinates x, y and z of the target point are calculated automatically by computer. These coordinates are mediated to motors which move the needle guide and thereby the needle. When the needle has been aligned, the motor which moves the needle vertically starts, and the specimen is taken automatically. However, this known method has the disadvantages of being expensive owing to its automation and motorization, and of being non-patient-friendly, since the patient has to be at the "mercy" of the machine and has to trust in automation, and this may, especially in older people, arouse repugnance against the examination.

SUMMARY OF THE INVENTION

The object of the present invention is to eliminate these disadvantages. The essential characteristics of the invention are stated in the accompanying claims.

In the method according to the present invention, a non-moving subject is radiographed from two angles by means of a rotating picture head, the projection angle being approximately $\pm 10°$, the pictures are placed on a separate measurement table, and the x-, y-, and z-coordinates of the desired site in the target are calculated in a known manner on the basis of the two pictures. Thereafter the measuring means on the measurement table are brought to the calculated x-, y-coordinates, and the detachable needle guide is placed in a fixed attachment means in the measurement table, and the needle guide is adjusted to these coordinates indicated by the measuring means. The z-coordinate is adjusted, for example, with the help of a scale in the needle guide. Thereafter the pre-adjusted needle guide is attached to the mammography apparatus and the specimen is taken by pressing the needle manually into the target.

A mathematical description of the calculation of the desired site in the target on the basis of a pair of pictures is presented, for example, in WO publication 88/01847.

The assembly according to the invention for thin needle biopsy in connection with mammography comprises: a mammography apparatus having a rotating picture head for taking a pair of pictures of the subject, from two angles; a detachable needle guide which can be attached to a fixed device in the mammography apparatus; a separate measurement table having measuring means by the use of which the x-, y-, and z-coordinates of the desired site in the target can be determined by calculation from the picture pair, in a manner known per se; and a fixed means in the measurement table for the needle guide in order to adjust the needle guide to the calculated coordinates. The essential idea is that the fixed attachment means in the measurement table and in the mammography apparatus are in the same position with respect to the calculated coordinates, in which case the needle guide can be transferred, preadjusted, from the measurement table to the attachment means in the mammography apparatus.

In order to localize a suspect site in a patient's tissue so that a thin needle biopsy specimen can be taken therefrom, the tissue in question is radiographed from two angles using a rotating picture head. The pictures so obtained are placed onto a separate measurement table, and the x, y, and z coordinates of the site to be located are then calculated in a known manner using the two pictures.

Measuring means on a measuring table are then brought to the x and y coordinates calculated as above, and a detachable needle guide is placed in a fixed attachment means in the measurement table. The needle guide is adjusted to these coordinates as indicated by the measuring means. For example, the z-coordinate is adjusted using a scale in the needle guide. After the needle guide is adjusted appropriately, the needle guide is attached to the mammography apparatus, the tissue in question is inserted into the mammography apparatus, and a specimen is taken by pressing the needle manually into the target.

The method and apparatus according to the invention are economical, since no expensive automation for moving and adjusting the needle guide is needed. Furthermore, the method and apparatus according to the invention are highly patient-friendly, since the needle guide is detachable, and thus the patient can be placed in the mammography apparatus without the needle, which horrifies some patients, being visible. In the method according to the invention the needle guide is pre-adjusted at the measurement table and is then transferred, pre-adjusted, to within the range of vision of the patient and is attached to the mammography apparatus.

The biopsy itself is carried out by pressing the needle downwards manually, at which time the presence of the person carrying out the operation, i.e. the so-called human factor, will arouse confidence in the patient.

BRIEF DESCRIPTION OF THE DRAWINGS

The invention is described below with reference to the FIGS, in which.

DETAILED DESCRIPTION OF THE INVENTION

Figure 1:
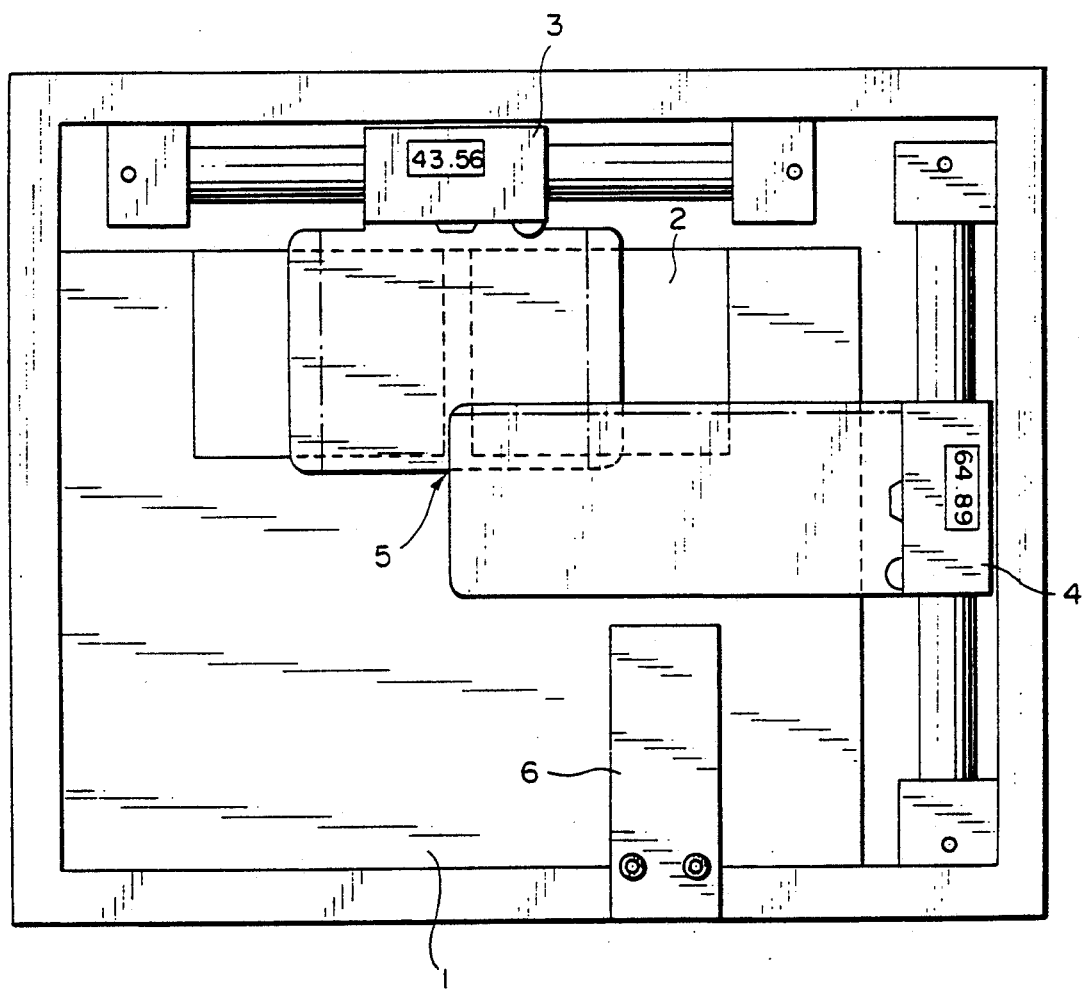
FIG. 1 depicts a measurement table by means of which the x-, y-, and z-coordinates of the target are determined.

The measurement table in FIG. 1 comprises a light table 1, on top of which a pair of pictures 2 taken from two different angles are placed. The intersection point 5 of the digital measuring sticks 3 and 4 is aligned with the target points in the pictures, and the coordinates of the desired point in the target are calculated by computer. At the edge of the measuring table there is installed a fixed attachment means 6 for attaching the needle guide. The measuring sticks 3 and 4 are placed at the x- and y-coordinates obtained from the computer, and according to these coordinates the x- and y-coordinates of the needle guide are set. The z-coordinate is adjusted, for example, by using a scale in the needle guide.

Figure 2:
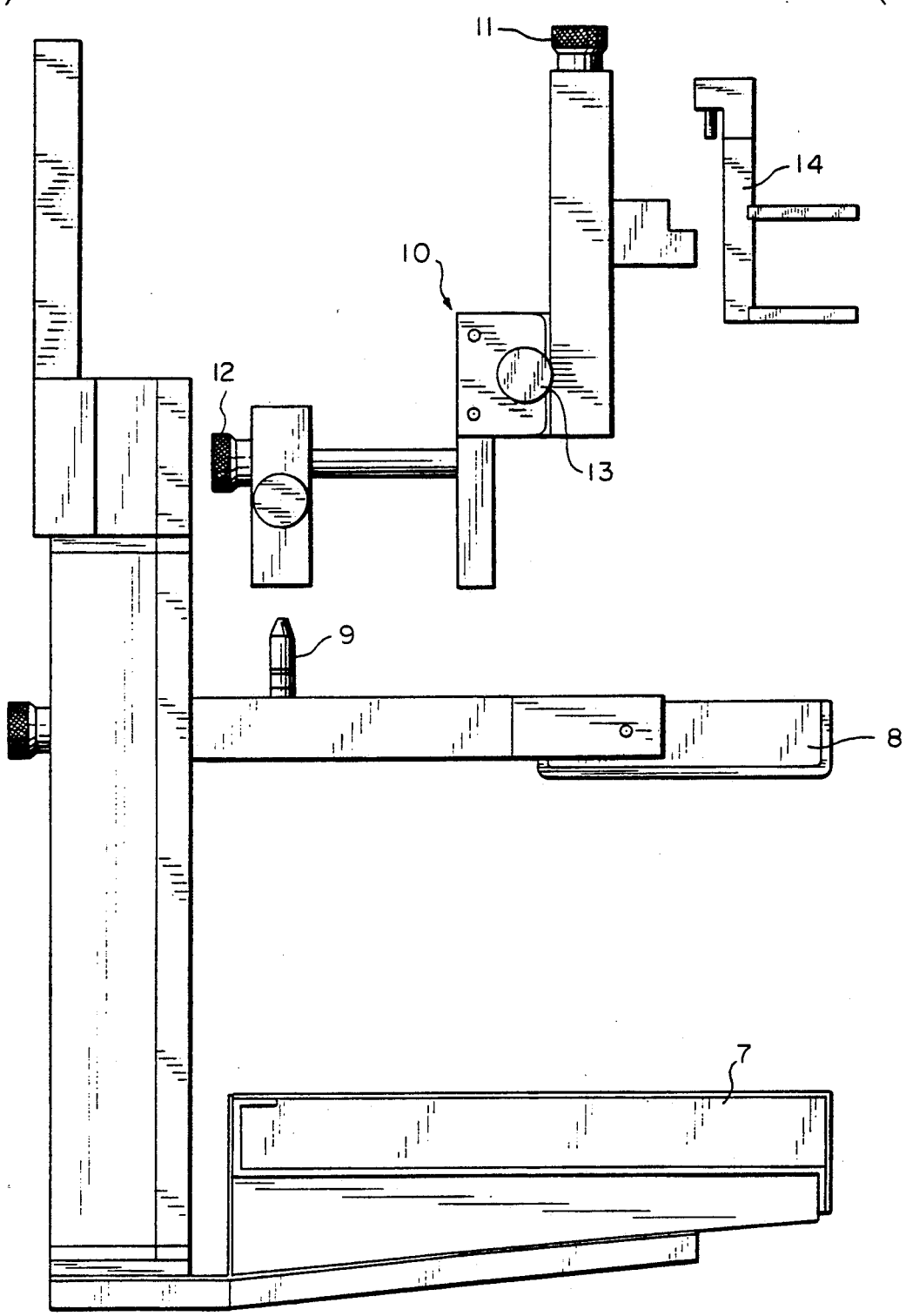
FIG. 2 depicts a portion of the mammography apparatus, with the needle guide and the needle holder.

FIG. 2 shows the cassette table 7 and the compression plate 8 of the mammography apparatus, there being in the compression plate a fixed attachment means 9 for attaching the needle guide 10. The target to be radiographed is placed between the cassette table 7 and the compression plate 8. The attachment means 9 is in the same position with respect to the x-, y- and z-coordinates as is the attachment means 6 on the measurement table. The needle guide has adjustment screws 11, 12 and 13 for adjusting the coordinates. The needle holder 14 is separate from the needle guide and can be mounted just before biopsy.

Figure 3:
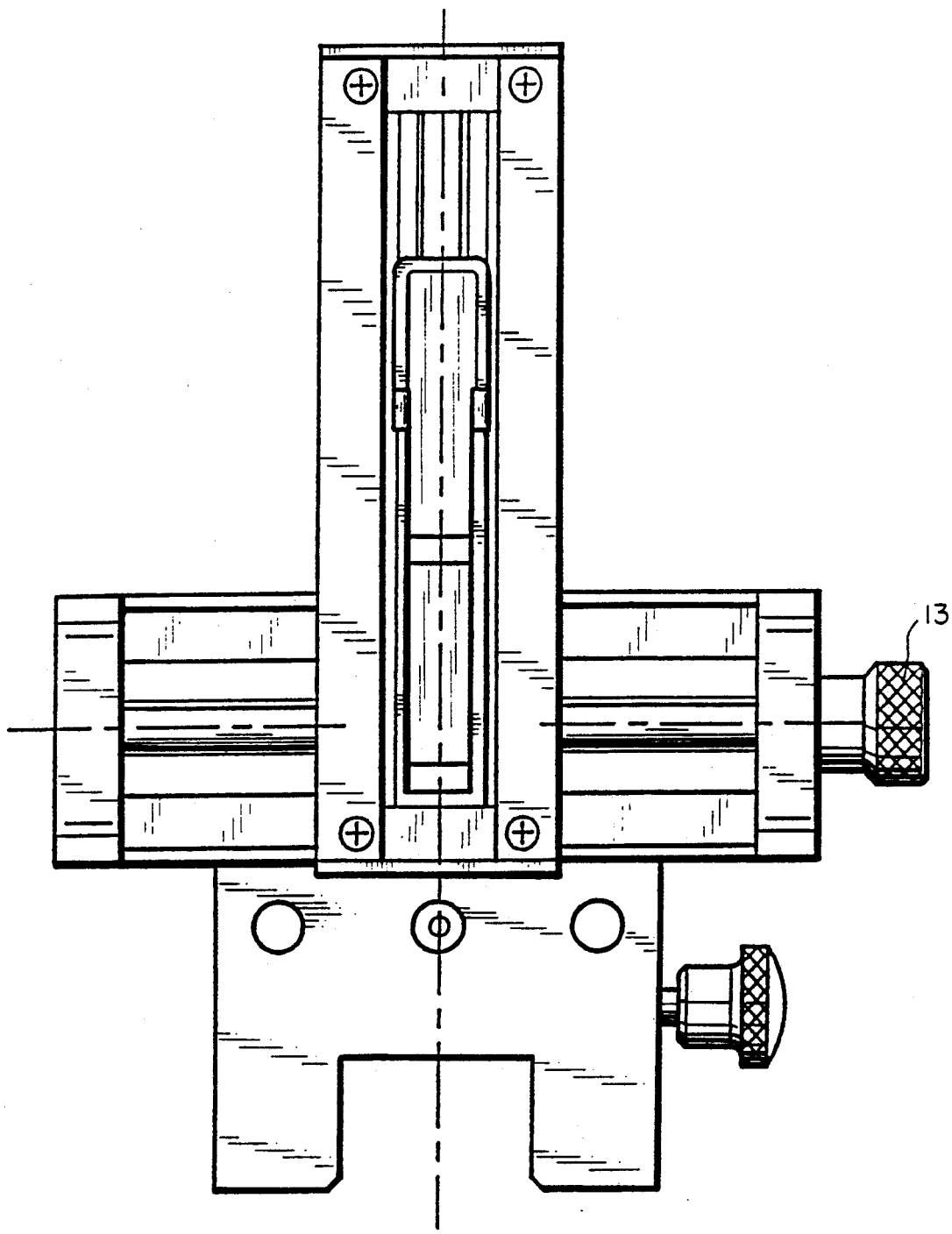
FIG. 3 depicts a front view of the needle guide with the needle holder.

FIG. 3 depicts a front view of the needle guide with the needle holder. The FIG. shows the adjustment screw 13 for the x-coordinate.

As shown in FIG. 1, the measurement table comprises a light table 1. Pictures taken from two different angles are placed on top of the light table 1. Two digital measuring sticks, 3 and 4, are provided to measure the target points on the pictures, and the intersection 5 of the two digital measuring sticks is obtained and the coordinates of the desired point in the target are calculated by computer. A fixed attachment means 6 is located at the edge of the measuring table, which fixed attachment means is used for attaching a needle guide.

FIG. 2 shows the cassette table, which is located beneath the compression plate 8 of a mammography apparatus. The compression plate includes a fixed attachment means 9 for attaching the needle guide 10. The target to be radiographed is placed between the cassette table 7 and the compression plate 8. The location of the attachment means 9 corresponds to the position of the attachment means 6 of the measurement table with respect to the x-, y-, and z-coordinates. Adjustment screws 11, 12 and 13 are provided on the needle guide to adjust the coordinates. The needle holder 14 is located separate from the needle guide, and can be mounted just prior to biopsy.

FIG. 3 shows a front view of the needle guide with the needle holder 14. The adjustment screw for the x-coordinate 13 is shown at the right of the needle guide.

We claim:

1. A method for locating a needle for thin needle biopsy comprising:
    radiographing a stationary target from two angles using a rotating picture head to obtain two pictures;
    placing said two pictures onto a measurement table;
    calculating the coordinates of the desired site in the target on the basis of the two pictures;
    providing a detachable needle guide on said measurement table and adjusting said needle guide in accordance with the calculated coordinates.

2. The method according to claim 1 wherein said adjusted needle guide is attached to a mammography apparatus such that said needle guide is attached in substantially the same direction as the manner in which said needle guide is attached to said measurement table with respect to said calculated coordinates to align the needle guide towards the desired site in the target.

3. An apparatus for locating a needle for thin needle biopsy comprising:
    a mammography apparatus, said mammography apparatus including a rotating picture head to obtain two pictures of a biopsy target;
    a detachable needle guide which can be attached to a fixed attachment means in said mammography apparatus;
    a separate measurement table, said separate measurement table having a fixed attachment means for said needle guide;
    measuring means on said measurement table for measuring and calculating coordinates of said biopsy target from said two pictures;
    wherein said fixed attachment means on said measurement table and said fixed attachment means on said mammography apparatus are located in the same position with respect to coordinates calculated from said two pictures of said biopsy target.

4. The apparatus according to claim 3 wherein the measuring means are digital.

* * * * *